Figure 1A:
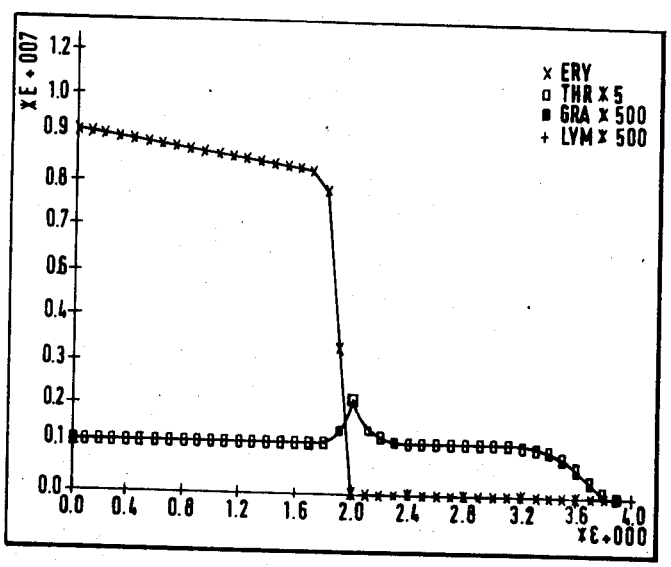

United States Patent [19]

Neumann et al.

[11] Patent Number: 4,675,117
[45] Date of Patent: Jun. 23, 1987

[54] METHOD OF SEPARATING BLOOD AND APPARATUS FOR CARRYING OUT THE METHOD

[75] Inventors: Hans-Jürgen Neumann; Artur Meisberger, both of St. Wendel; Wolfram Weber, Spiesen, all of Fed. Rep. of Germany

[73] Assignee: Fresenius AG, Bad Homburg, Fed. Rep. of Germany

[21] Appl. No.: 713,746

[22] Filed: Mar. 20, 1985

[30] Foreign Application Priority Data

Mar. 21, 1984 [DE] Fed. Rep. of Germany ....... 3410286

[51] Int. Cl.⁴ ............................................. B01D 21/26
[52] U.S. Cl. ................................... 210/789; 210/194; 210/378; 210/805; 210/927
[58] Field of Search ..................... 494/10, 43; 210/194, 210/196, 322, 360.1, 378, 512.1, 787, 789, 805, 927, 782

[56] References Cited

U.S. PATENT DOCUMENTS

| | | | |
|---|---|---|---|
| 3,489,145 | 1/1970 | Judson et al. | 494/10 X |
| 3,955,755 | 5/1976 | Breillatt, Jr. et al. | 494/10 X |
| 3,957,197 | 5/1976 | Sartory et al. | 494/10 X |
| 4,007,871 | 2/1977 | Jones et al. | 210/789 X |
| 4,010,894 | 3/1977 | Kellogg et al. | 210/927 X |
| 4,146,172 | 3/1979 | Cullis et al. | 494/45 X |
| 4,151,844 | 5/1979 | Cullis et al. | 210/927 X |
| 4,330,080 | 5/1982 | Mathieu | 494/43 |
| 4,530,691 | 7/1985 | Brown | 210/927 X |
| 4,531,932 | 7/1985 | Luppi et al. | 210/927 X |

FOREIGN PATENT DOCUMENTS

| | | |
|---|---|---|
| 2354368 | 5/1974 | Fed. Rep. of Germany . |
| 2624154 | 5/1977 | Fed. Rep. of Germany . |
| 2821057 | 1/1979 | Fed. Rep. of Germany . |
| 2845399 | 4/1979 | Fed. Rep. of Germany . |
| 2845364 | 4/1979 | Fed. Rep. of Germany . |
| 2821055 | 4/1979 | Fed. Rep. of Germany . |
| 2925010 | 1/1980 | Fed. Rep. of Germany . |
| 2612988 | 12/1982 | Fed. Rep. of Germany . |

Primary Examiner—Richard V. Fisher
Assistant Examiner—W. Gary Jones
Attorney, Agent, or Firm—Cushman, Darby & Cushman

[57] ABSTRACT

Method of separating blood, in particular for recovering thrombocytes and/or leucocytes, the whole blood coming from the donor being separated in a separation means of a centrifuge into an erythrocyte fraction, cell-poor plasma, a thrombocyte fraction and/or possibly a leucocyte fraction, the separated fractions of the blood being discharged via a flexible tubing system of discharge lines out of the separation chambers of the centrifuge and constantly predetermined amounts of separated cell-poor plasma returned to the whole blood to be separated or to the already separated erythrocytes in the separation chamber, and a separation apparatus for carrying out the method comprising a separator having one or more separating chambers connected together and a flexible tubing system which includes a supply line (1, 2) for the supply of the whole blood to be separated to the separator and discharge lines each for the separate discharge of the erythrocyte fraction (10), the cell-poor plasma (3, 5), the thrombocyte fraction (11) and/or possibly leucocyte fractions and a branch line (7) disposed on the output side from the separator in the discharge line (3) for cell-poor plasma for returning cell-poor plasma, the supply and discharge lines and the branch lines (7) of the flexible tubing system being equipped with pumps, and the branch line (7) disposed on the output side of the separator is led off between the separator and the pump (6) and the pump (8, P) diposed in the branch line (7) delivers a predetermined plasma amount.

12 Claims, 11 Drawing Figures

METHOD OF SEPARATING BLOOD AND APPARATUS FOR CARRYING OUT THE METHOD

The present invention relates to a method of separating blood, in particular for recovering thrombocytes and/or leucocytes, the whole blood coming from the donor being separated in a separation means of a centrifuge into an erythrocyte fraction, cell-poor plasma, a thrombocyte fraction and/or possibly a leucocyte fraction, the separated fractions of the blood being discharged via a flexible tubing system of discharge lines out of the separation chamber and separated cell-poor plasma being partially returned, and an apparatus for carrying out the method.

Various methods and apparatuses are already known for separating whole blood into its various components, an in-vivo blood treatment being carried out in that blood is taken from a donor or patient, separated in a separation apparatus of a centrifuge into all or some of its components, i.e. erythrocytes, leucocytes, thrombocytes and plasma, and one or more of the components to be recovered removed from the system whilst the remaining blood plasma is returned to the donor or patient. Examples of such methods and apparatuses for carrying them out are described in DE-OS No. 2,845,399, DE-OS No. 2,845,364, DE-OS No. 2,821,057, DE-OS No. 2,624,154, DE-OS No. 2,821,055, DE-OS No. 2,925,010, DE-OS No. 2,354,368, DE-PS No. 2,612,988, US-PS No. 3,955,755, US-PS No. 3,957,197, US-PS No. 4,007,871, US-PS No. 4,010,894, US-PS No. 4,146,172, US-PS No. 4,330,080 and US-PS No. 3,489,145.

In the separation of blood components with a centrifuge apart from the plasma separation the thrombocyte and leucocyte separation represent important fields of use. In cell separation, i.e. erythrocyte, leucocyte (granulocyte and lymphocyte) or thrombocyte separation, the patient or donor is connected via one or two connections with his brachial vein for several hours, typically one to three hours, by means of a tubing system to the separator of a centrifuge. The cell yield, i.e. the total number of cells of the particular type desired collected from the blood, is limited essentially by the maximum flow of the whole blood which is in turn limited by the maximum venous flow of the patient of typically 50–80 ml/min., and the efficiency of the separator of the centrifuge. All hitherto known methods and commercially available cell separation apparatuses have the disadvantage that their efficiency and thus also the cell yield is low consequently considerable expenditure is involved in obtaining the desired cell separation and the patient or donor must be subjected to a great strain in order to arrive at the desired result. This disadvantageous strain is firstly due to a long treatment time with simultaneous pronounced circulation stress and secondly to damage to the blood components returned to the patient.

There is therefore an urgent need for new methods and apparatuses with improved efficiency in cell recovery and less disadvantageous effects on the blood.

In the methods hitherto known an increase in the efficiency is aimed at only by optimum adjustment of the phase boundaries arising in the centrifugation between individual cell types. The phase boundaries are to be adjusted as well as possible to spatially predetermined separation means for the fractions. Possibilities of doing this are manual regulation of the ratio plasma flow to erythrocyte flow as described in US-PS No. 3,489,145 and PCT/US No. 81/01096, and an automatic or semi-automatic control of the plasma pump, as described in US-PS No. 4,146,172, US-PS No. 3,955,755 and DE-PA No. 33 01 113.3.

The method according to US-PS No. 3,957,197 is also to be seen under this aspect: the ratio plasma flow to erythrocyte flow in this case is set by regulating the hematocrit value of the blood reaching the centrifuge to a constant and defined value.

The method according to this U.S. patent is therefore carried out in that by means of continuous electrical conductivity measurements the hematocrit value of the whole blood in the charging line is measured and the hematocrit value of the entering whole blood by adding a separated fraction (plasma fraction or erythrocyte fraction) from the corresponding lines via an exactly regulated pump (pump 7) to the charging line for the whole blood is regulated to a predetermined value.

The problem underlying the present invention is to provide a method and apparatus with which it is possible by simple means to obtain any desired in particular low hematocrit value of the whole blood entering the separating chamber of the centrifuge and thus to increase the efficiency in cell recovery and simultaneously reduce the detrimental effects on the blood.

The method according to the invention is characterized in that predetermined cell-poor plasma amounts are returned.

According to the invention the method is carried out in that the whole blood coming from the donor or patient, possibly correspondingly pretreated (i.e. e.g. mixed with anticoagulant) is introduced via a charging or supply line into a separation chamber of a centrifuge and there separated in one or more separation chambers (depending on the type of separator used), for example one or two chambers, of centrifugal force corresponding to the specific weight of the blood components into an erythrocyte fraction, cell-poor plasma, a thrombocyte fraction and/or possibly leucocyte fractions (granulocytes and lymphoctes). Via discharge lines the individual fractions are then separately removed from the separator, which is done in the usual manner possibly employing regulatable pumps, preferably hose pumps. The cell-poor plasma is also removed from the separation chamber via a discharge line or a discharge passage, and between the cell separation part of the centrifuge and in front of the (regulatable) plasma pump provided for conducting away the plasma a branch is provided via which a portion of the cell-poor plasma is led to a further line and there returned with constant flow to the whole blood by means of a constantly driven pump, i.e. a pump delivering constantly defined amounts.

According to the method of the invention the cell-poor plasma can also be returned to the separated erythrocytes in the separator in the same manner as explained above.

The term "cell-poor plasma" used here means a plasma which collects in the separation method and depending on the cell type to be recovered, e.g. leucocytes and/or thrombocytes, is leucocyte-poor, i.e. a plasma which collects in leucocyte recovery and from which the leucocytes are removed, or is thrombocyte-poor, i.e. a plasma which collects in the thrombocyte recovery and from which substantially all blood cells have been removed.

The method according to the invention is based on the principle of dilution.

This is done in simple manner by merely adding to the known separation apparatuses for separating blood a simple additional means such as for example an additional pump hose with a constantly driven pump. Such an additional means can be used in all known systems and apparatuses for separating blood, i.e. including those described in the aforementioned prior art publications, provided that they have the aforementioned tubing system including supply or discharge lines. This additional means is disposed at the discharge line for the cell-poor plasma from the separator downstream, i.e. on the output side, in such a manner that it is in the portion of the discharge line which lies between the separator and the plasma pump or plasma feed pump. It may be a conventional hose or flexible tube portion which is connected at one end in usual manner to the discharge line for the cell-poor plasma, is connected to a constantly driven pump delivering predetermined amounts and at the other end is connected in conventional manner to the charging or supply line for the whole blood. Through said hose portion part of the cell-poor plasma is returned in constant flow to the whole blood. It is however also possible to connect the other end of the hose portion not to the supply line for the whole blood but to the part of the separation chamber in which the separated erythrocytes are disposed and thus return a portion of the cell-poor plasma in constant flow to the erythrocytes disposed in the separator.

The former of the aforementioned embodiments has the practical advantage of not having to lead any additional connections or tubes into the centrifuge or out of the latter.

The material for the additional means is substantially the same material used for the other supply or discharge lines, i.e. the other parts of the tubing system, and is preferably plastic compatible with blood.

The separation apparatus used according to the invention may have one or more separation chambers, for example one or two chambers, which are connected to each other in conventional manner, for example via connecting lines.

The flexible tubing or hose system according to the invention includes the supply or charging line for the whole blood, the discharge lines with regulatable pumps for carrying away the separated blood components, such as erythrocytes, thrombocytes and cell-poor plasma and possibly leucocytes (granulocytes, lymphocytes) and the additional means (pump hose, hose and constantly driven pump) for returning the separated cell-poor plasma, one end of which is connected downstream of the separator to the discharge line for the plasma and the other end of which is connected either to the supply or charging line for the whole blood or to the part of the separator in which separated erythrocytes are disposed. The connection of the tubing system to the separator on the one hand and to the donor or patient on the other is in the usual manner.

With the method according to the invention and the apparatuses according to the invention it is surprisingly possible in simple manner to increase the efficiency of the cell separator and thus the cell yield by the factor of about 1.5 compared with hitherto known commercially available methods and apparatuses and at the same time to handle all blood components during the separation very carefully, i.e. to impair as little as possible the functionability. Furthermore, with the procedure according to the invention (dilution) the apparatus is made less sensitive.

Although hereinafter the method and apparatuses or systems are explained with reference to thrombocyte recovery, it is of course obvious that the method according to the invention and the apparatuses can be applied in similar manner also to the recovery of other blood cells, such as leucocytes, e.g. lymphocytes and granulocytes.

For the two-stage method frequently used for cell separation, in particular for thrombocyte recovery, in the first stage the thrombocyte-rich plasma (PRP) is separated from the rapidly settling erythrocytes (RBC); in the next stage the thrombocytes (PLT) still in the plasma are recovered (by centrifugation and possibly by filtration).

The following equations apply to the thrombocyte flow according to the first stage:

$$N_{PLT} = Q_{PRP} \cdot n_{PRP}$$

$N_{PLT}$ = (Thrombocyte) flow (particles /time)
$Q_{PRP}$ = Flow of the (thrombocyte-rich) plasma (Volume /time)
$n_{PRP}$ = (Thrombocyte) density in the PRP (particle /volume).

The round brackets in the definitions are intended to show that these equations also apply to different cell types, for example leucocytes.

The plasma flow results from the volume flow $Q_{WB}$ and the hematocrit value HK:

$$Q_{PRP} = Q_{WB} \cdot (1 - HK) \qquad (2)$$

$$Q_{WB} = Q_{WB}(1 - HK) + Q \cdot HK \qquad (3)$$

The equation (3) applies for complete sedimentation of the RBC in the centrifuge and (1) thus becomes:

$$N_{PLT} = Q_{WB} \cdot (1 - HK) \cdot n_{PRP} \qquad (4)$$

Since the sedimentation range of the erythrocytes is very large compared with that of the thrombocytes, the physical parameters of the centrifuge ($Q_{WB}$ radius, speed, chamber volume) can be chosen such that the erythrocytes are sedimented but the thrombocytes are still substantially in the initial uniform distribution n (ignoring for clarity in this case further effects such as dynamic flow behavior, swarm prevention of the cells among each other and the bouyancy of the very light thrombocytes).

We then have:

$$n_{PRP} = n_{WB}$$

$n_{WB}$ = (thrombocyte) density in the whole blood (particles /volume)

$$N_{PLT} = Q_{WB}(1 - HK) \cdot n_{WB} \qquad (5)$$

It is obvious that with this method the thrombocytes included by the erythrocytes cannot be recovered; this loss fraction is proportional to the hematocrit value HK set (cf. FIG. 1).

If therefore the hematocrit value in equation (5) is reduced by adding a dilution, the maximum thrombocyte flow $n_{PLT}$ which can be achieved increases (for the same whole blood flow $Q_{WB}$) A practical embodiment of the diultion to be made is a continuous return of part of the separated thrombocyte-poor plasma (PPP). This plasma available after the second separation stage is either returned to the whole blood (WB) or to the erythrocytes (RBC). This means a corresponding reduction of the hematocrit value HK.

With the return equation (5) becomes $$N_{PLT} = [Q_{WB}(1 - HK) + Q_{rück}] \cdot n_{WB} \left( \frac{Q_{WB}}{Q_{WB} + Q_{rück}} \right) \quad (6)$$

If the physical parameters of the centrifuge are so designed that sedimentation of the erythrocytes is possible in spite of the increase in the centrifuge throughput $$Q_Z = Q_{WB} + Q_{rück}$$

then the improvement V in the thrombocyte yield is:

$$V = \frac{[Q_{WB} \cdot (1 - HK) + Q_{rück}] \cdot n_{WB} \cdot \left( \frac{Q_{WB}}{Q_{WB} + Q_{rück}} \right)}{Q_{WB} \cdot (1 - HK) \cdot n_{WB}} \quad (7)$$

If the plasma is for example returned in the ratio 1:1 with the whole blood ($Q_{rück} = Q_{WB}$) then with $$\left. \begin{array}{l} HK\ 0.5\ \text{(whole blood)} \\ Q_{rück} = Q_{WB} \end{array} \right\} \text{ with equation (7) } V = 1.5$$

With still higher dilutions as limit value an improvement at the most of a factor of 2 is possible, i.e. 100% PLT is then recovered.

If the return is not to the whole blood in front of the separation chamber but to the erythrocyte (RBC) lying separately in the first stage in the separation chamber a higher improvement factor is obtained with the same return amount. However, this means that an additional supply to the separation chamber is necessary.

Of course, an increase of the centrifuge throughput $Q_Z$ $$Q_Z = Q_{WB} + Q_{rück}$$

means at the same time a reduction in the sedimentation time, i.e. the residence time of a particle in the centrifuge. A high dilution therefore comes up against the technical limit of the centrifuge performance, i.e. the residence time becomes shorter than the necessary sedimentation time.

A plasma return of 1:1 represents a comprise here which is also easy to realise technically. The residence time is reduced by the factor 2 and simultaneously however the necessary sedimentation time for the erythrocytes is reduced by $\triangleq 2$ so that a complete sedimentation takes place in the same centrifuge with the same physical conditions.

A dilution of the blood to be separated by the apparatus according to the invention has the further advantage that for a high cell yield the hematocrit value of the erythrocytes to be returned may be smaller than without this apparatus. From the physiological point of view a high hematocrit value is detrimental to the viability of the erythrocytes or of all the cells. By combinations of these two advantages depending on the intention operation settings may be combined:

rapid=high hematocrit value of the returned erythrocytes conservative=low hematocrit value of the returned erythrocytes In general, separated thrombocyte-poor plasma is returned in a ratio to the whole blood to be separated in an amount in the range from 25%, 75% to 90%:10%, preferably in the range 40%:60% to 75%:25%, in particular 1:1 to 1:2, i.e. about 50%:50% to 66%:33%. In the return of the separated cell-poor or thrombocyte-poor plasma to the separated erythrocytes disposed in the separator the ratio of the returned plasma to the erythrocytes is about 62.5%:37.5% to 95%:5%, preferably 70%:30% to 87.5%:12.5%, and in particular is about 75%:25%.

This principle of plasma return is also applicable to other types of cells (leucocytes (WBC), granulocytes) (in this case for example with additives of usual sedimentation accelerators for the erythrocytes, for example HES (hydroxyethyl starch), polysaccarides (dextrans), oxypolygelatins, methylprednisolone or mixes thereof) because here as well the efficiency of the cell yield is limited by the components included by the erythrocytes. These sedimentation accelerators give reversible microaggregates which sediment better. A dilution by plasma return leads here to the same improvements as in equation (7). The recovery of these types of cell is either in a two-stage method or the cells are recovered after completed sedimentation in the separation boundary.

Since the principle of plasma return does not function until the "run-in" state, i.e. after adequate plasma separation according to equation (7), the automatic control of the phase boundary (DE-PA No. 33,01,112.3) used in the system by means of the plasma feed pump is an obvious solution. The method is of course also combinable with other methods for regulating the phase boundary.

Figure 1B:
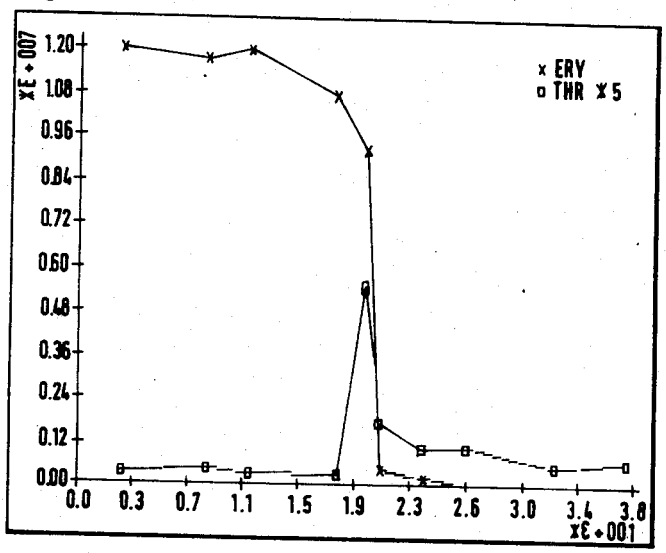
Figure 2A:
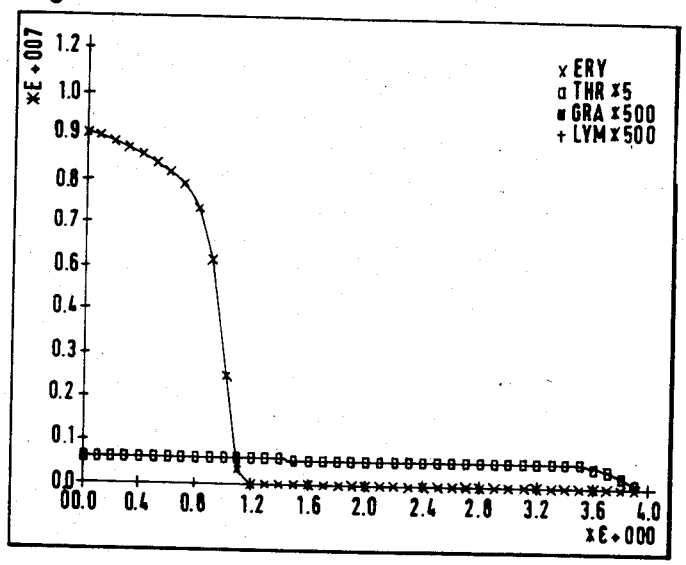
Figure 2B:
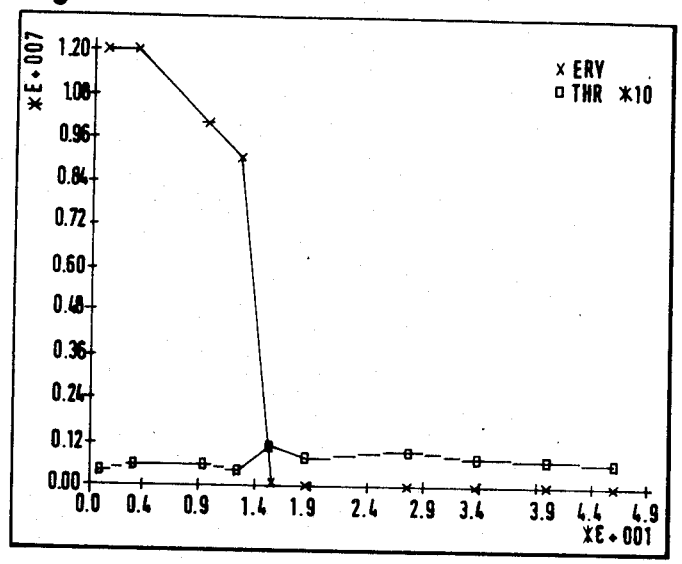
Figure 3:
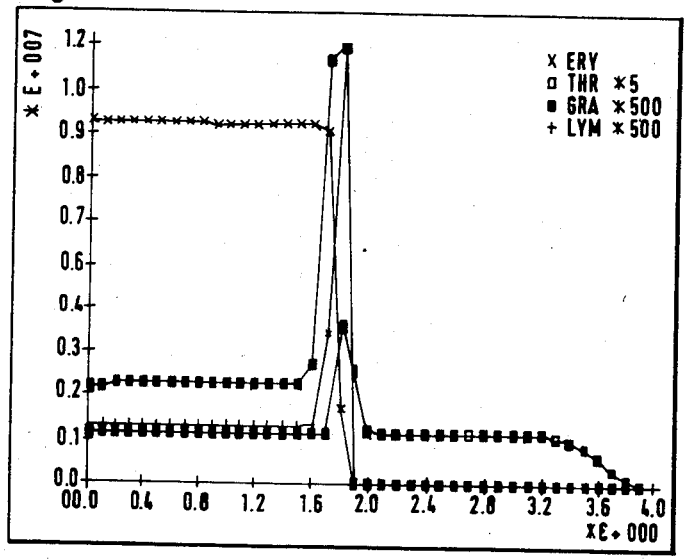
Figure 4:
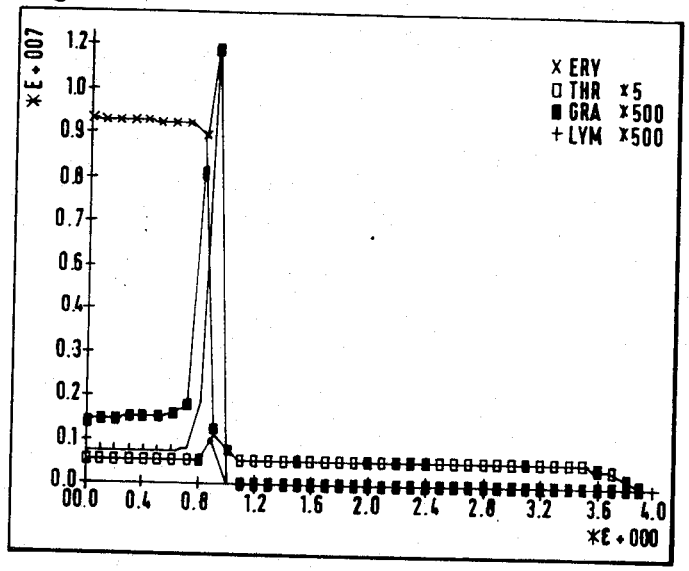
Figure 5A:
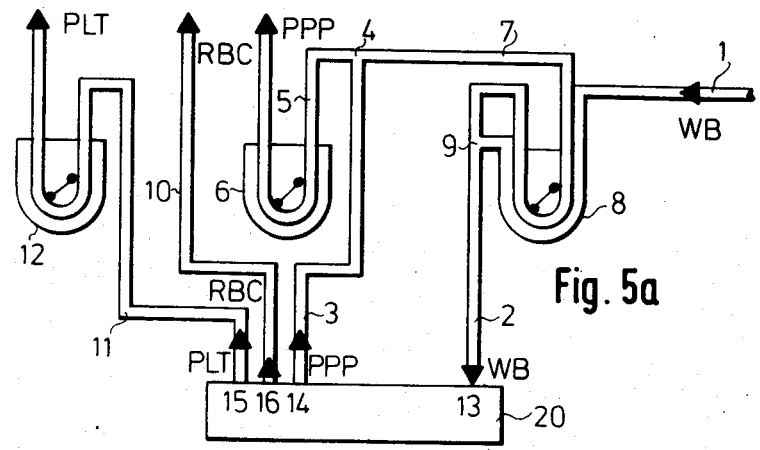
Figure 5B:
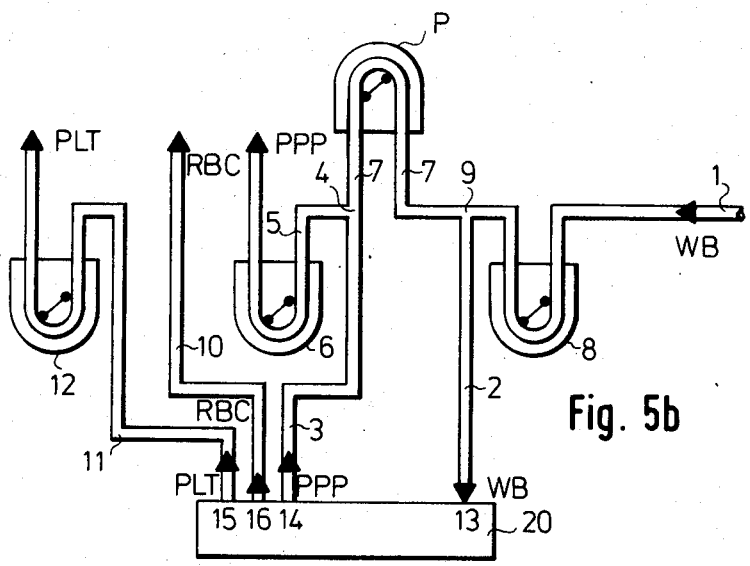
Figure 6A:
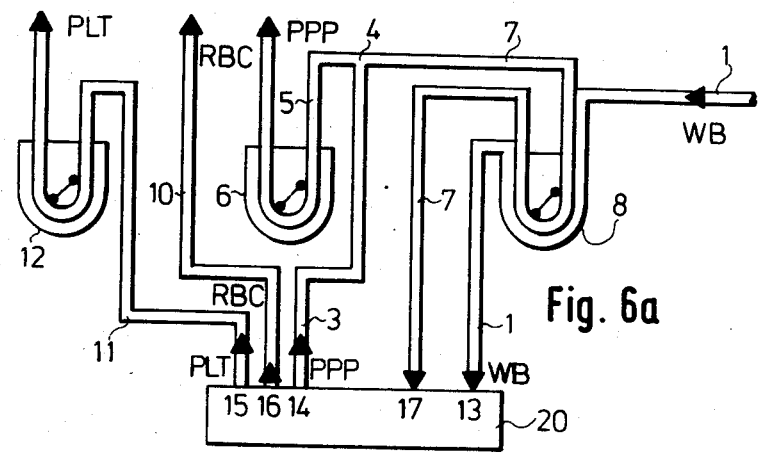
Figure 6B:
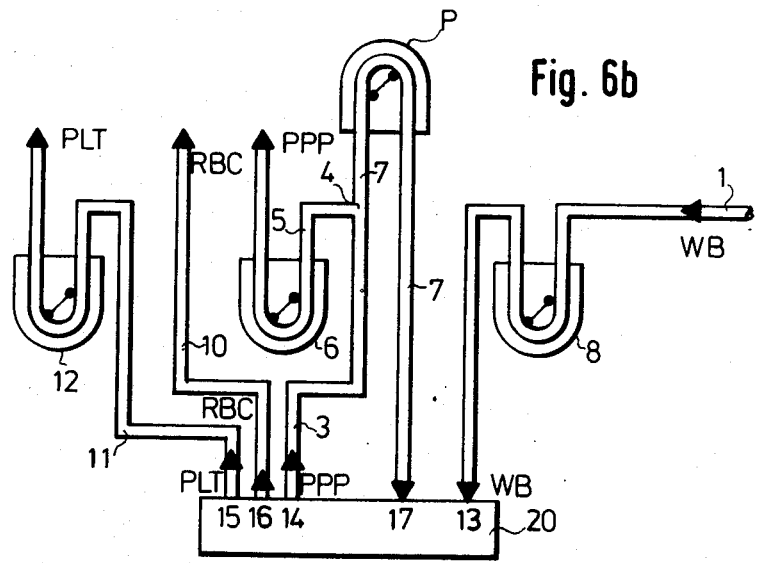
Figure 7:
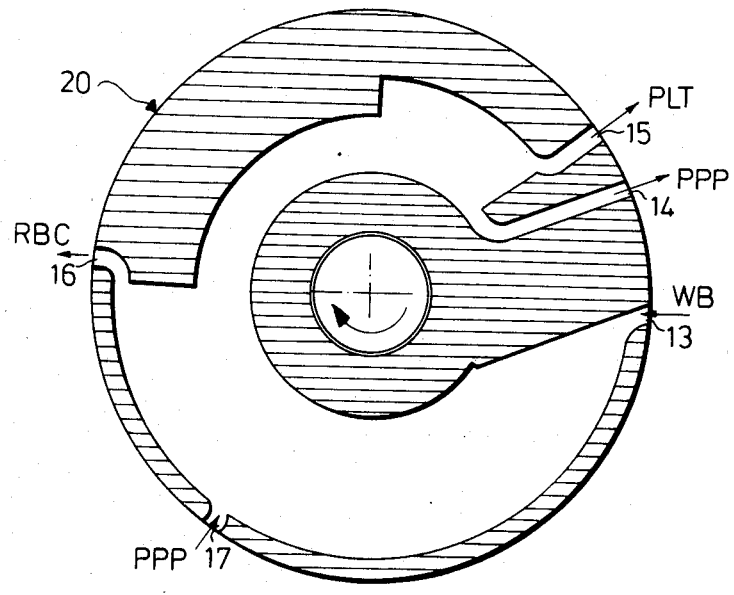

The present invention will be explained hereinafter with reference to the drawings, wherein:

FIG. 1a is a graphic representation of the sedimentation profile of whole blood (computer simulation analogous to equations 1–6), FIG. 1b is a graphic representation of the sedimentation profile of whole blood analogous to FIG. 1a in accordance with measurements on whole blood with ACD (anti coagulant), FIG. 2a is a graphic representation of the sedimentation profile according to the method of the invention with plasma feedback or return, FIG. 2b is a graphic representation of the sedimentation profile in accordance with measurements on dilutions whole blood:plasma=1:1, FIG. 3 is a graphic representation of the sedimentation profile of whole blood analogous to FIG. 1, also considering granulocytes and lymphocytes, FIG. 4 is a graphic representation of the sedimentation profile of whole blood, also considering granulocytes and lymphocytes, in accordance with the method of the invention with plasma return, FIG. 5a is a schematic representation of the principle according to the invention of plasma return to the whole blood outside the centrifuge, FIG. 5b is a schematic representation of the principle according to the invention of plasma return outside the centrifuge analogous to FIG. 5a but with separate pump (P), FIG. 6a is a schematic representation of the principle according to the invention of plasma return outside the centrifuge to separated erythrocytes disposed in the centrifuge, FIG. 6b is a schematic representation of the principle according to the invention of plasma return analogous to FIG. 6a but with separate pump (P), FIG. 7 is a sectional view of a separation chamber with plasma return to the separated erythrocytes according to FIG. 6a and 6b but without lines.

In FIG. 1a the concentration of the cells is represented as a function of the radial sedimentation path, i.e. chamber depth, after the first separation stage. The thrombocytes (<2 mm) lying beneath the erythrocytes are substantially lost for the cell recovery in second stage.

The thrombocytes lying above (>2 mm) the erythrocytes are recovered in the second separation stage with a percentage of 47.8 (of the whole blood).

In FIG. 2a the advantage obtainable according to the invention by plasma return in apparent. With the same chamber and same whole blood flow (50 ml/min) as with the method used in FIG. 1a but with plasma feedback, in spite of the plasma return of 1:1 and the resulting shortening of the residence time (½) the erythrocytes are almost completely sedimented.

The improvement of the thrombocyte recovery to 70.1% represents a factor of 1.47 which is in good agreement with the theoretical results according to citation (7).

In FIGS. 1b and 2b the observations in FIGS. 1a and 2a are confirmed by measurements. The percentage of the cell proportion lying beneath the erythrocytes is numerically somewhat different from that in FIGS. 1a and 2a which can be explained by the simplified observation in FIGS. 1a and 2a. The improvement of the cell proportions with plasma return is however very good qualitatively.

According to the graphic representation of the sedimentation profile of whole blood illustrated in FIG. 3 compared with FIG. 1 the granulocytes and lymphocytes have also been considered. In addition, the operation was with a sedimentation accelerator for the erythrocytes (HES). The cells form a layer on the erythrocytes and can be removed therefrom.

FIG. 4 shows the improvement obtainable by the plasma return according to the invention compared with the results illustrated in FIG. 3; the operation was carried out with the same separation chamber and the same whole blood flow. For what the thrombocyte recovery the plasma return means an improvement of 54.8% to 77.2%. The improvement for the cell recovery also relates to the other blood cells contained in the whole blood. In this case, instead of a second sedimentation stage the cells can be removed directly at the cell boundary.

In FIG. 5a the centrifuge separator is shown only schematically because the method according to the invention can be carried out with any separator, irrespective of its construction and irrespective of whether one or more separation chambers are present, provided that the supply lines and discharge lines illustrated in FIG. 5 are present. For example, the separation apparatuses described in DE-OS No. 2,845,399, DE-OS No. 2,845,364, DE-OS No. 2,821,057, DE-OS No. 2,624,154, DE-OS No. 2,821,055, DE-OS No. 2,925,010, DE-PS No. 2,612,988, US-PS No. 4,330,080 and US-PS No. 3,955,755 can be used.

1 and 2 denote in FIG. 5 the supply (or charging) lines for the whole blood (WB). Via the line 3 the cell-poor or thrombocyte-poor plasma (PPP) is discharged from the separator. At 4 this line 3 divides into a line in which said cell-poor or thrombocyte-poor plasma is led to a hose pump (plasma pump) 6 and from there discharged or supplied to the donor, and a line 7 which together with the line 1 carrying the whole blood is placed in the double hose pump 8 (which can also deliver various quantities depending on the respective hose cross-section) and downstream of the pump 8 is combined at the branch 9 with the line 1. The whole blood mixed with the feedback plasma is then led via the line 2 to the separation chamber where it is subjected to the possibly two-stage separation method described above. Via the line 10 the erythrocytes (RBC) and via the line 11 and the pump 12 the thrombocytes (PLT) are removed.

In contrast to the other pumps of the system, i.e. pumps 6 and 12, the pump 8 is not regulatable but is driven constantly and constantly delivers predetermined amounts.

Although in the aforementioned FIG. 5a the cell-poor or thrombocyte-poor plasma is supplied to the whole blood before reaching the separator chamber by means of the double hose pump 8 it is alternatively possible to use a separate constantly diven pump as illustrated in FIG. 5b. The reference numerals used in FIG. 5b correspond substantially to those used in FIG. 5a with the exception that in FIG. 5b the constantly driven pump delivering predetermined amounts is denoted by P. The procedure corresponds to that explained for FIG. 5a; as in the latter, according to FIG. 5b as well the returned plasma (PPP) is combined in the whole blood to be separated at 9.

In the method according to the invention the backflow rate is completely non-critical. It may have any desired magnitude and can be kept constant. Furthermore according to the invention measurements of input quantities are not necessary.

According to the invention the system starts up automatically and after the starting the recirculation of the plasma does not impair the separation and the separation boundary between the thrombocytes and the red blood corpuscles remains at the same point if the capacity of the centrifuge suffices for complete separation of the additional volume.

Analogous to FIGS. 5a and 5b, in FIGS. 6a and 6b the centrifuge or separator is shown only schematically. FIGS. 6a and 6b differ from FIGS. 5a and 5b essentially in that the return of the separated plasma is not to the whole blood but to the separated erythrocytes disposed in the separator. For the same parts in FIGS. 6a and 6b the same reference numerals as in FIGS. 5a and 5b are used. Thus, in FIG. 6a, 1 and 2 denote the supply (or charging) lines for the whole blood (WB), the whole blood being introduced through the opening 13 into the centrifuge or separator 20. Via the line 3 the cell-poor or thrombocyte-poor plasma (PPP) is discharged through the opening 14 from the separator. At 4 the line 3 divides into a line 5 in which said cell-poor or thrombocyte-poor plasma is led to a hose pump (plasma pump) 6 and from there discharged or led to the donor, and a line 7 in which part of the thrombocyte-poor plasma is led firstly to a double hose pump 8 which can also deliver different quantities depending on the respective hose cross-section and then introduced at the opening 17 into the separator radially from the outside and combined with the separated erythrocytes. Through the opening 16 the erythrocytes (RBC) are discharged from the separator and then removed via the line 10. The thrombocytes (PLT) are discharged from the separator through the opening 15 and then removed via the line 11 and the pump 12.

In contrast to the other pumps of the system, i.e. the pumps 6 and 12, the pump 8 is not regulatable but is driven constantly and delivers constant predetermined amounts.

Although in the aforementioned FIG. 6a the cell-poor or thrombocyte-poor plasma is supplied by means of the double hose pump 8 to the separator through the opening 17, it is however also possible to use a separate constantly driven pump as illustrated in FIG. 6b. The reference numerals used in FIG. 6b correspond substantially to the reference numerals used in FIG. 6a with the exception that in FIG. 6b the constantly driven pump delivering predetermined amounts is denoted by P. The procedure corresponds to that indicated for FIG. 6a. As in the latter according to FIG. 6b as well the returned plasma (PPP) is introduced through the opening 17 to the part of the separator in which the already separated erythrocytes are disposed.

FIG. 7 shows a section through a separation chamber 20; thrombocyte-poor plasma separated in accordance with the procedure of the invention is returned to the separated erythrocytes in the separation chamber. Through the opening 13 the whole blood to be separated is introduced into the separation chamber where firstly the erythrocytes separate and then in the segments of smaller radius the second stage of the separation takes place, i.e. the separation of the thrombocyte-reduced plasma into thrombocytes and thrombocyte-poor plasma. Through the opening 14 the thrombocyte-poor plasma is removed and through the opening 15 the thrombocyte fraction. The plasma returned according to the invention as described in FIGS. 6a and 6b passes radially from the outside through the opening 17 into the separation chamber to the separated erythrocytes. The separated erythrocytes are removed through the opening 16. As illustrated in FIGS. 6a and 6b in this case as well all the openings in the separation chamber are connected according to the supply and discharge lines. In the same manner, the opening 17 is connected to the supply line 7 and the constantly driven pump 8 or P.

Instead of the dilution of the entire whole blood in this case in accordance with FIGS. 6a, 6b and 7 only a dilution of the erythrocytes takes place and as a result for the same amount of returned plasma the improvement factor V (see equation (7)) becomes greater compared with the factor obtained according to the method illustrated in FIGS. 5a and 5b.

The region around the opening 17 may optionally additionally be designed as a mixing chamber.

The recovery of the leucocytes itself can be carried out in the usual manner but in accordance with the invention as described above cell-poor plasma is returned. The aforementioned particulars given for thrombocyte recovery are applicable to leucocyte recovery in a similar manner with appropriate modification.

Thus, the leucocyte recovery can be carried out essentially in that firstly from the whole blood the erythrocytes are sedimented with the aid of usual sedimentation accelerators (such as HES). The leucocytes can then deposit on the erythrocytes as layer and from there withdrawn directly at the separating boundary. The cell-poor (leucocyte-poor, thrombocyte-rich) plasma can then be removed as described above and/or possibly separated in a further separation stage into thrombocytes and thrombocyte-poor (cell-poor) plasma. The cell-poor plasma is then partially turned as set forth above.

It is however also possible to adopt the procedure that as described above from the whole blood by means of usual sedimentation accelerators firstly the erythrocytes are separated, the cell-rich plasma separated in the next separating stage into leucocytes and cell-poor (leucocyte-poor) plasma and then a part of the cell-poor plasma returned in accordance with the invention in the manner described. Possibly, in a further separation stage the cell-poor plasma can be separated into thrombocytes and thrombocyte-poor plasma and then again in accordance with the invention part of the cell-poor (thrombocyte-poor) plasma returned.

We claim:

1. Method of separating whole blood coming from a donar for recovering at least one of thrombocytes and leucocytes, comprising the steps of:
    separating the whole blood in a separation means of a centrifuge having separation chambers into an erythrocyte fraction, cell-poor plasma, and at least one of a thrombocyte fraction and a leucocyte fraction;
    discharging the separation fractions of the blood via a flexible tubing system of discharge lines out of the separation chamber of the centrifuge; and
    returning a constant amount of the separated cell-poor plasma to the separation means, said constant amount being defined by a non-regulatable pump means operatively coupled to a discharge line of separated plasma.

2. Method according to claim 1, wherein the cell-poor plasma is returned to the whole blood to be separated.

3. Mcthod according to claim 2, wherein the plasma is returned to the whole blood before introduction into the separation chamber.

4. Method according to claim 1, wherein the plasma is returned in the ratio of 40% 60% to 75% : 25% with respect to the whole blood to be separated.

5. Method according to claim 1, wherein the plasma is returned to the separated erythrocytes in the separation chamber.

6. Method according to claim 5, wherein the plasma is returned in the ratio of 70% : 30% to 87.5% : 12.5% with respect to the separated erythrocytes.

7. Method according to claim 5 wherein the plasma is returned in the ratio of 75%:25% with respect to the separated erythrocytes.

8. Method according to claim 1 wherein the plasma is retruned in the ratio of 1:1 to 2:1 with respect to the whole blood to be separated.

9. Apparatus for separating whole blood coming from a donor for recovering at least one of thrombocytes and leucocytes comprising:
    means for separating the whole blood into an erythrocyte fraction, cell-poor plasma, and at least one of a thrombocyte fraction and leucocyte fractions;
    said means for separating having at least one separating chamber, said chambers being connected together
    a flexible tubing system which includes a supply line to conduct the whole blood to be separated to the separator, discharge lines for the separate discharge of each of the erythrocyte fraction, the cell-poor plasma, the thrombocyte fraction and leucoctye fraction and a branch line disposed in the discharge line for cell-poor plasma for returning cell-poor plasma to the means for separating, the supply, discharge and branch lines of the flexible tubing system each being operatively coupled to a pump, the pump of the branch line being non-regulatable so as to return a constant amount of plasma.

10. Apparatus according to claim 9, wherein the supply and discharge lines are operatively coupled to regulatable pumps.

11. Apparatus according to claim 9 or 10, wherein the branch line is connected to the supply line for the whole blood to be separated downstream of the pump of the whole blood supply line.

12. Apparatus according to claim 9 or 10, wherein the branch line is conaected to the part of the separation chamber in which separated erythrocytes are disposed.

* * * * *